US007755368B2

(12) United States Patent
Herrmann et al.

(10) Patent No.: US 7,755,368 B2
(45) Date of Patent: Jul. 13, 2010

(54) METHOD AND DEVICE FOR MEASURING MASS AND/OR MOISTURE OF THE CONTENT OF CAPSULES

(75) Inventors: Rainer Herrmann, Hamburg (DE); Udo Schlemm, Hamburg (DE)

(73) Assignee: TEWS Elektronik Dipl.-Ing. Manfred Tews, Hamburg (DE)

(*) Notice: Subject to any disclaimer, the term of this patent is extended or adjusted under 35 U.S.C. 154(b) by 291 days.

(21) Appl. No.: 11/702,973

(22) Filed: Feb. 6, 2007

(65) Prior Publication Data

US 2008/0186031 A1    Aug. 7, 2008

(51) Int. Cl.
G01R 27/04    (2006.01)
(52) U.S. Cl. .................. 324/634; 324/636; 324/640
(58) Field of Classification Search ............ 324/634, 324/637
See application file for complete search history.

(56) References Cited

U.S. PATENT DOCUMENTS 5,397,993 A * 3/1995 Tews et al. ............... 324/634
5,554,935 A * 9/1996 Kraszewski et al. ........ 324/637
5,602,485 A * 2/1997 Mayer et al. .............. 324/663
5,977,780 A * 11/1999 Herrmann ................. 324/634
7,042,231 B2 * 5/2006 Trebbi .................... 324/637
7,071,706 B2 * 7/2006 Mueller .................. 324/637
7,337,074 B2 * 2/2008 Herrmann et al. ........... 702/23
2004/0225454 A1 * 11/2004 Herrmann et al. ........... 702/23

FOREIGN PATENT DOCUMENTS

| EP | 0 889 321 A1 | 1/1999 |
| EP | 1 467 191 A1 | 10/2004 |
| EP | 1 484 586 A1 | 12/2004 |
| WO | WO 2004/005903 A1 | 1/2004 |

* cited by examiner

*Primary Examiner*—Timothy J Dole
(74) *Attorney, Agent, or Firm*—Alix, Yale & Ristas, LLP

(57) ABSTRACT

A Method and an apparatus for measuring the mass and/or moisture of the contents of incompletely filled capsules, containing, in particular, medicinal products, pharmaceutical products, vitamins and similar products, with the aid of microwaves is disclosed. The displacement of the resonant frequency and broadening of the resonance curve caused by the capsules in at least one resonator is determined and evaluated. Measurements are made integrated over the whole capsule as well as with high local resolution for various portions and cross sections of the capsule.

25 Claims, 5 Drawing Sheets a)

b)

Position perpendicular to measuring tube in mm

METHOD AND DEVICE FOR MEASURING MASS AND/OR MOISTURE OF THE CONTENT OF CAPSULES

BACKGROUND

The invention relates to a method for measuring the mass and/or moisture of the contents of capsules, containing, in particular, medicinal products, pharmaceutical products, vitamins and similar products, with the aid of microwaves, in which method the displacement of the resonant frequency and broadening of the resonance curve caused by the capsules in a resonator is determined and evaluated, and to an apparatus for carrying out the method.

Such a method can be used to determine the mass and/or moisture of portioned active ingredient units, in particular also capsules (EP 1 467 191 A1). If the weight of the capsule casing is known, by establishing the difference the mass of the contents of the capsule, which contains, in particular, medicinal products, pharmaceutical products, vitamins or similar products, is obtained. If, however, the mass of the contents of the capsule is substantially less than the mass of the capsule casing, non-uniform masses of the capsule casings lead to considerable errors when determining the mass of the contents. An exemplary capsule has a mass of 50 mg, while the mass of the capsule contents, comprising carrier material and active ingredient, is 5 mg. This typical example alone shows that, if the capsule mass varies by +/−5 mg, a measurement of the mass of the contents on ready filled capsules is no longer possible, even if the overall accuracy of the measurement is less than 0.5 mg. It is particularly important, however, especially with small amounts of ingredients and active ingredients, to know the amount contained in the capsule. For this purpose, the capsule could, for example, be weighed before and after filling. However, apart from the fact that this necessitates intervention in the filling machine, the mechanical operation of weighing always requires a certain amount of time, so that many balances would have to be arranged parallel to one another to obtain a sufficiently high throughput. A further example involves the measurement of the total mass of the empty and filled capsule in the region of the filling machine by two appropriately arranged microwave measuring systems (EP 1467191 A1).

SUMMARY

Briefly stated, one method provides for the checking measurement of ready filled capsules, with which mass and/or moisture of the capsule contents can be measured quickly and reliably.

One disclosed method comprises in determining not only the total mass and/or total moisture of the filled capsule, but, with further measurements of the capsule, in determining and evaluating the differing interaction of the individual parts of the capsule with electromagnetic fields.

These further measurements are localised. They therefore do not measure the total values of the filled capsule, but values at specific points.

For instance, the moisture of the capsule casing can be determined with the aid of electromagnetic fields. This measurement is in most cases sufficient, since the moisture of the capsule contents is either zero or else these capsule contents always have the same moisture. The mass of the contents of the capsule can then be determined from the measured values.

In one embodiment, the moisture of the capsule casing can be determined with infrared radiation. Since this only has a certain penetration depth, the measured value is influenced only by the moisture of the capsule casing, but not by the moisture of the capsule contents. At zero moisture of the contents or a known constant moisture value, the mass of the capsule contents can then again be determined.

In an alternative embodiment, the moisture of the capsule casing is determined with the aid of microwaves in a resonator having a measuring volume which is so severely limited that only a part of the capsule casing without contents can be detected therewith. Only the capsule casing then influences the measured value. If the moisture value of the capsule casing is determined in this way, at zero moisture or a known constant moisture of the contents the mass of the contents can again be determined.

In many, if not the majority of cases, the contents do not completely fill the capsule. In this case, it is possible, to determine the mass of the contents, even if the moisture thereof varies and is not known. This can be achieved, in one embodiment, by the contents of the capsule being transported to one side of the capsule cavity by acceleration or gravity, and the moisture of the capsule being determined with the aid of microwaves as a function of the measuring point over the length of the capsule. Not only the total mass and the total moisture of the filled capsule is thus determined here in a homogeneous measuring field, but also the moisture as a function of the measuring point over the length of the capsule. Profile sensors which enable measurement over a relatively small measuring volume are known for this (EP 0 889 321 A1).

On the side of the capsule on which the contents are situated, the microwave signal is influenced by the moisture of the capsule casing and the moisture of the capsule contents, while on the other side, on which no contents are situated, the microwave signal is only influenced by the moisture of the capsule casing. In this case, it is possible to determine moisture of capsule and contents and, on the other hand, only of the capsule casing separately from one another. From this, the mass of the contents can again be determined.

This measurement can be carried out by using a first resonator with a measuring field which is homogeneous over the capsule dimensions to determine the total mass/moisture of the capsule and by using a second resonator with a narrow measuring field (profile sensor) to determine location-dependent mass/moisture values. It is then merely to be ensured here that the measurements in the two resonators are assigned to the same capsule. The order here is not important. The measurement can take place firstly in the homogeneous measuring field and then in the profile sensor, or vice versa.

The measurements can, however, also be carried out with only one resonator having a narrow measuring field (profile sensor). In this case, the total mass/moisture is determined by integration of the individual values determined over the length of the capsule. To this end, it is necessary for the capsules to be moved through the measuring volume at the same speed.

In another embodiment of similar structure, the capsule is not moved through the measuring volume at the same speed, but the speed at which the capsule moves through the measuring field is measured in each case.

The measurements are advantageously carried out at a microwave frequency of 1 to 50 GHz, in particular 1 to 5 GHz.

A apparatus may also be employed for carrying out the methods.

BRIEF DESCRIPTION OF THE DRAWINGS

FIG. 4a shows a microwave sensor with a measuring field, which sensor can be used for a method;

FIG. 4b shows the microwave field strength over the length extent of the resonator of FIG. 4a;

DETAILED DESCRIPTION

Figure 1:
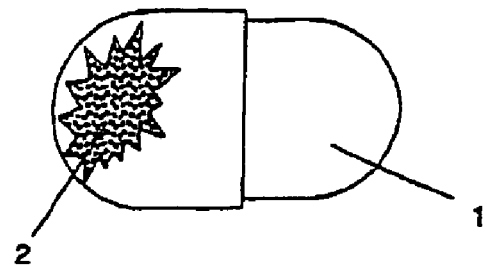
FIG. 1 shows a diagram of a capsule with its contents.

In the case of a microwave resonance method, two resonance parameters are measured during each measurement. The first of the measured quantities is the displacement of the resonant frequency A in Hz:

$$A = f_0 - f_m \quad (1)$$

where $f_0$: is the resonant frequency of the empty resonator in Hz $f_m$: is the resonant frequency of the filled resonator in Hz.

The second measured quantity is the enlargement of the half-width of the resonance B in Hz:

$$B = w_m - w_0 \quad (2)$$

where $w_0$: is the half-width of the resonance of the empty resonator in Hz $w_m$: is the half-width of the resonance of the filled resonator in Hz Since both parameters A and B are equally mass-dependent, the quotient of the two quantities is mass-independent. The mass-independent microwave moisture value F is obtained from this quotient as follows:

$$F = \arctan(B/A) \quad (3)$$

By measuring the two parameters A and B, it is possible, besides determining the moisture of the object to be measured, also to determine the mass of the object to be measured, provided that the measuring field in which the object to be measured is homogeneous.

When measuring the contents of filled capsules, the following characteristic quantities are unknown:

1. The mass of the capsule casing $m_k$
2. The mass of the contents $m_i$
3. The mass of the water in the capsule casing $m_{wk}$
4. The mass of the water in the capsule contents $m_{wi}$ In practice, the mass of the water in the capsule contents $m_{wi}$ is often equal to zero or is constant, and therefore does not need to be determined in many measuring applications. Since, therefore, 3 or 4 characteristic quantities are unknown, 3 or 4 independent quantities need to be measured in order to be able to determine the mass of the capsule contents $m_i$. Various possibilities for realising this measurement are explained below.

1. Combination of an Integrating Microwave Resonator with a Resonator for Profile Measurement An integrating microwave resonator is understood to mean a resonator having a measuring field of constant field strength, which field is at least as large as the object to be measured. The object to be measured must be situated completely within this homogeneous measuring field during measurement. The resonance quantities $A_{int}$ and $B_{int}$ measured here are in this case dependent on mass and moisture fractions of the capsule casing and the contents:

$$A_{int} = a_1 \cdot m_k + a_2 \cdot m_i + a_3 \cdot m_{wk} + a_4 \cdot m_{wi} \quad (4)$$

$$B_{int} = b_1 \cdot m_k + b_2 \cdot m_i + b_3 \cdot m_{wk} + b_4 \cdot m_{wi} \quad (5)$$

Figure 2:
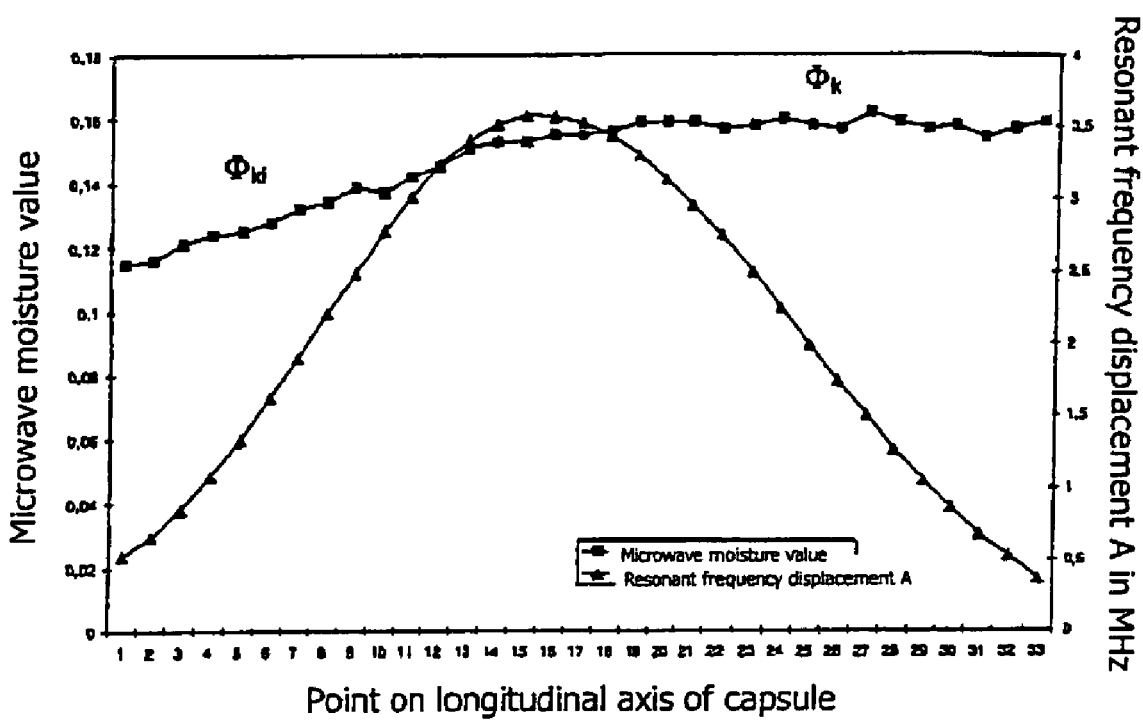
FIG. 2 shows the measured microwave moisture value and the resonant frequency displacement over the length extent of the capsule of FIG. 1.

Designations:

$A_{int}$: resonant frequency displacement through entire capsule $B_{int}$: broadening of the resonance curve through entire capsule $m_k$: mass of the capsule casing $m_i$: mass of the capsule contents $m_{wk}$: mass of the water in the capsule casing $m_{wi}$: mass of the water in the capsule contents $a_i$, $b_i$: coefficients A microwave resonator for profile measurement enables measurement of profiles of moisture and mass with a local resolution which is substantially less than the longitudinal extent of the object to be measured, in this case typically $\leq 3$ mm. TEWS Elektronik has already applied for a patent for such a profile resonator, under number EP 0 889 321 A1. When measuring partially filled medicinal capsules, it is to be ensured that, on guidance of the capsules, the capsule contents 2 are situated at one end of the capsule 1 owing to inertial or gravitational forces, as shown in FIG. 1. This can be achieved by strong acceleration or vertical positioning. For this case, FIG. 2 shows, by way of example, the measured profiles of the displacement of the resonant frequency A using relation (1) and of the microwave moisture value F according to relation (3) (capsule size 5, filling: 94 mg maize meal). From the left-hand region of the profile of the microwave moisture value F, the common microwave moisture value of capsule contents and capsule casing $F_{ki}$ can be determined. In the right-hand profile region the capsule casing is empty, so that the microwave moisture value of the empty capsule $F_k$ can be determined here.

For these values the following relations apply:

$$F_k = c_1 \cdot m_{wk}/(m_{wk} + m_k) + c_2 \quad (6)$$

$$F_{ki} = F_k + d_1 \cdot m_{wi}/(m_{wi} + m_i) + d_2 \quad (7)$$

Designations:

$F_{ki}$ microwave moisture value of capsule contents and capsule casing $F_k$: microwave moisture content of the empty capsule $m_k$: mass of the capsule casing $m_i$: mass of the capsule contents $m_{wk}$: mass of the water in the capsule casing $m_{wi}$: mass of the water in the capsule contents $c_i$, $d_i$: coefficients The coefficients $a_i$, $b_i$, $c_i$ and $d_i$ can be determined by calibration measurements. There thus exists a set of four measured quantities, from which the four unknown quantities mentioned above can be determined and thus also the sought mass of the capsule contents $m_i$. For this, it is necessary to solve the linear system of equations consisting of relations (4)-(7).

In the case, frequently occurring in pharmaceutical practice, where the capsule contents do not absorb any moisture, or the latter does not vary, only determination of three quantities to be measured is required: the resonant frequency displacement and the broadening of the resonance curve through the entire capsule, i.e. $A_{int}$ and $B_{int}$, as well as the microwave moisture value of the empty capsule $F_k$. This results in a reduced system of equations for determining the mass of the capsule contents $m_i$:

$$A_{int}=a_1 \cdot m_k + a_2 \cdot m_i + a_3 \cdot m_{wk} \quad (8)$$

$$B_{int}=b_1 \cdot m_k + b_2 \cdot m_i + b_3 \cdot m_{wk} \quad (9)$$

$$F_k = c_1 \cdot m_{wk}/(m_{wk}+m_k) + c_2 \quad (10)$$

Figure 3:
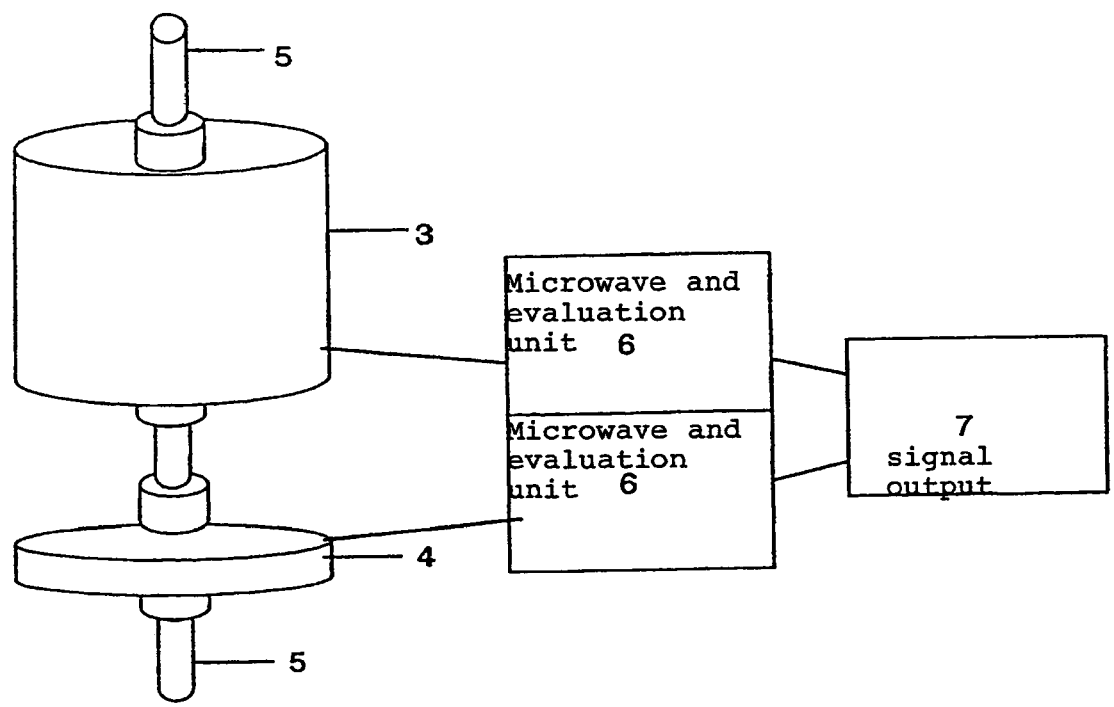
FIG. 3 shows a first measuring apparatus with which a method can be carried out.

Designations:
- $A_{int}$: resonant frequency displacement through entire capsule
- $B_{int}$: broadening of the resonance curve through entire capsule
- $F_k$: microwave moisture content of the empty capsule
- $m_k$: mass of the capsule casing
- $m_i$: mass of the capsule contents
- $m_{wk}$: mass of the water in the capsule casing
- $a_i$, $b_i$, $c_i$: coefficients An apparatus for carrying out this method is shown in FIG. 3. It has a microwave resonator 3, with a measuring field which is homogeneous at least over the capsule volume, and a profile sensor 4, which has a very narrow measuring field of the order of 3 mm in the direction in which the capsules move. Running through the resonators 3, 4 is a tube 5, through which the capsules to be measured are passed. The signals are evaluated in microwave and evaluation units 6 and the measurement results are calculated and displayed, printed out or documented in some other way by a unit 7.

Figure 8:
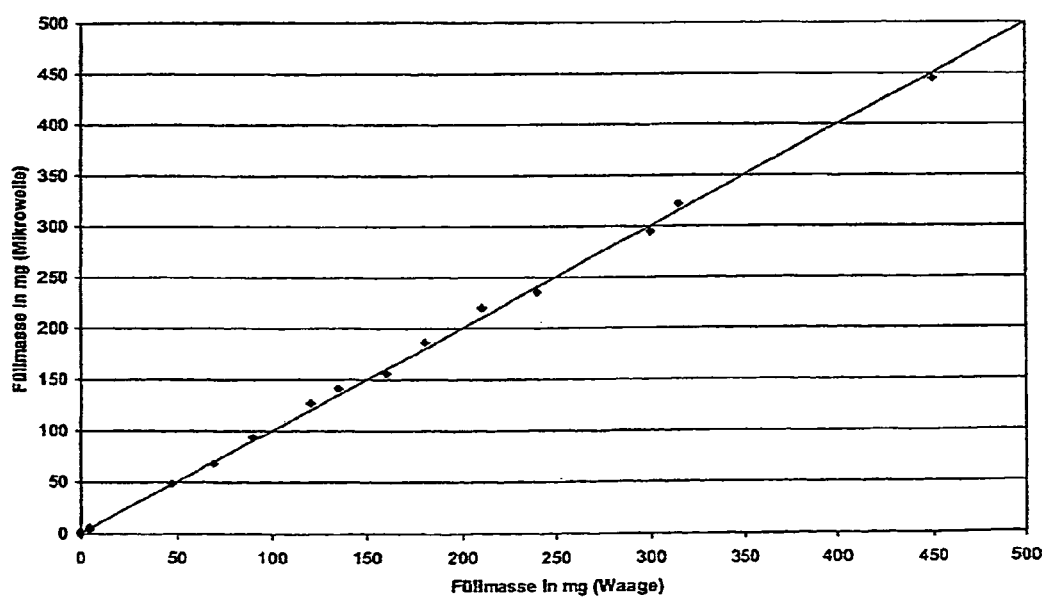
FIG. 8 shows a graph of the mass of the contents determined with a method as a function of the filling mass determined by a balance, for different capsule sizes.

FIG. 8 shows measurement results which were obtained using a combination of an integrating microwave resonator with a resonator for profile measurement on partially filled hard gelatin capsules, where greatly varying capsule sizes from 0 to 5 and filling amounts from 0 to 450 mg were used. As can be seen, the method for determining the mass of the contents is thus independent of the capsule size.

In the case of completely filled capsules, the moisture of the capsule casing cannot be determined by a profile measurement, and thus the determination of the mass of the contents fails. Since, however, with complete filling it holds that $m_k < m_i$ and the variations of $m_k$ are markedly less than $m_i$, the determination of the mass of the capsule contents can be determined in general with sufficient accuracy via the total mass of the capsule while taking into account an average value of the masses of the capsule casings. For this, measurement using an integrating microwave resonator is sufficient, cf. TEWS patent application "Method and apparatus for determining the mass of portioned active ingredients" EP 1 467 191 A1.

Figure 4:
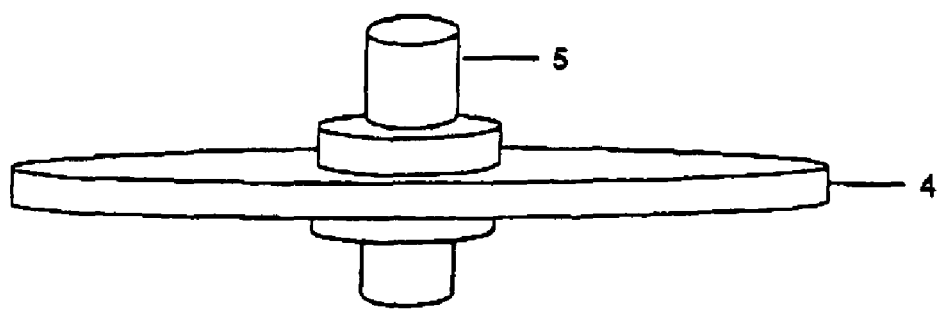
Figure 4:
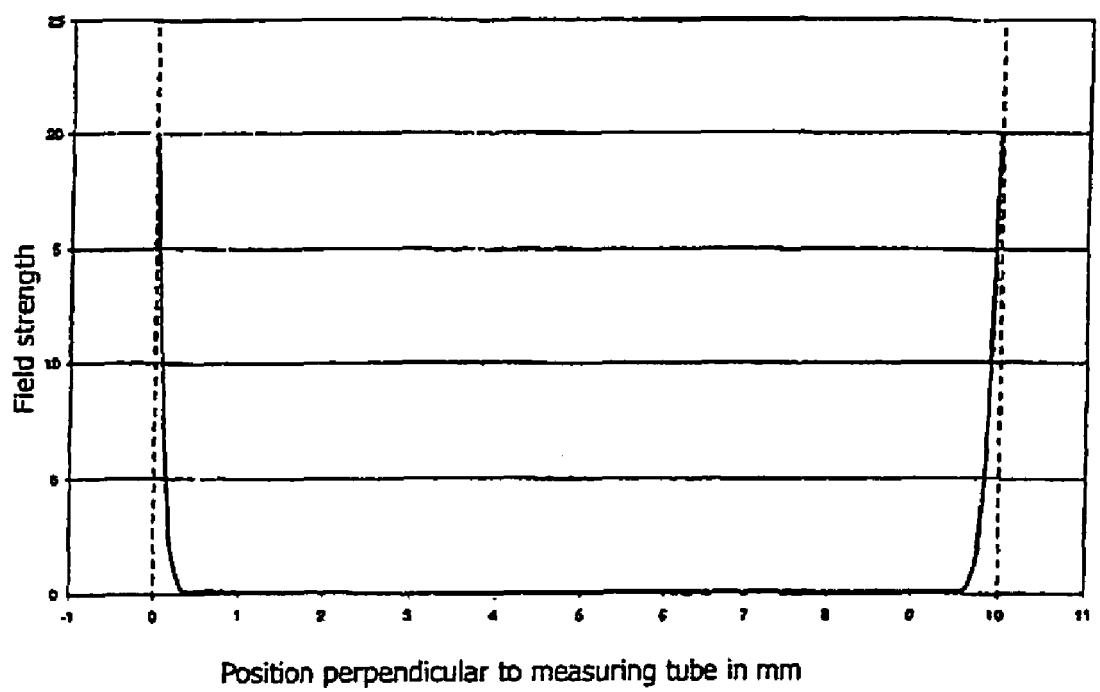
Figure 5:
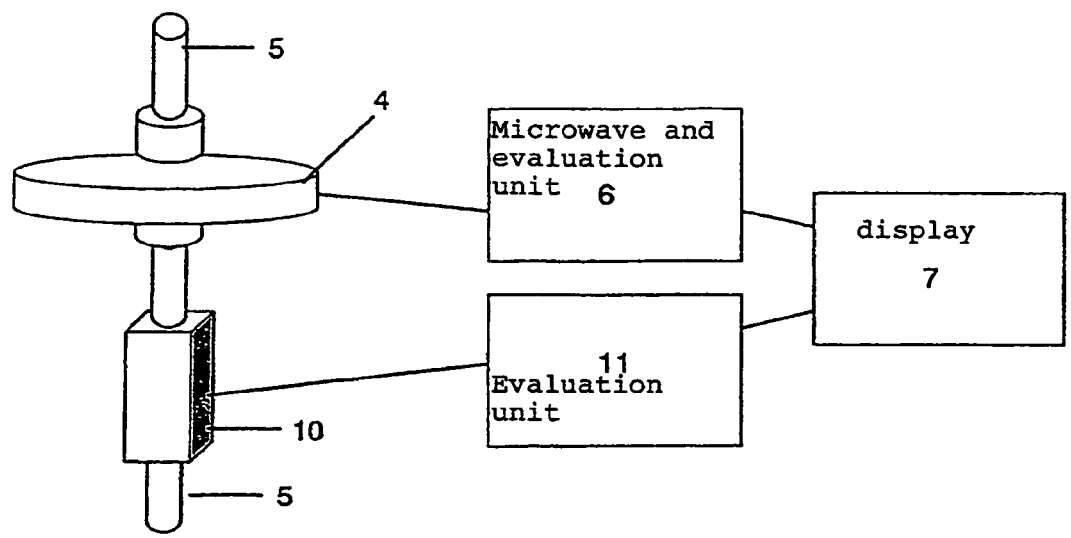
FIG. 5 shows another apparatus with which a method can be performed.

2. Combination of an Integrating Microwave Resonator with a Resonator for Measuring the Surface Moisture A microwave resonator for measuring the surface moisture has a measuring field which, only at the surface of the object to be measured, has a field strength suitable for the measurement, i.e. the properties of the object to be measured can be measured only at its surface. An example of such a resonator 4 is illustrated in FIG. 4. Such a resonator can be used to measure the microwave moisture value of the empty capsule $F_k$. In this case, too, the resonant frequency displacement and the broadening of the resonance curve through the entire capsule, i.e. $A_{int}$ and $B_{int}$, are measured by the integrating microwave resonator. A measurement on capsules with contents of varying moisture is not possible in this case. To evaluate the measurements, the system of equations (8)-(10) has to be solved. FIG. 3 schematically shows the structure of a measuring system which can be used for this case. These measurements can also be carried out when the capsules are completely filled.

3. Combination of an Integrating Microwave Resonator with a Moisture Measurement of the Capsule Casings Even with an infrared moisture-measuring system, given all the disadvantages of the infrared moisture-measuring technique, it is possible to measure the moisture of the capsule casings as in the aforementioned method independently of that of the filling material, since a surface measurement is involved here. Such a measurement would result in a moisture measured value corresponding to the above-described microwave moisture value of the empty capsule $F_k$. In this case, too, the resonant frequency displacement and the broadening of the resonance curve through the entire capsule, i.e. $A_{int}$ and $B_{int}$, are measured by the integrating microwave resonator. A measurement on capsules with contents of varying moisture is, however, not possible in this case. To evaluate the measurements, the system of equations (8)-(10) has to be solved.

Figure 7:
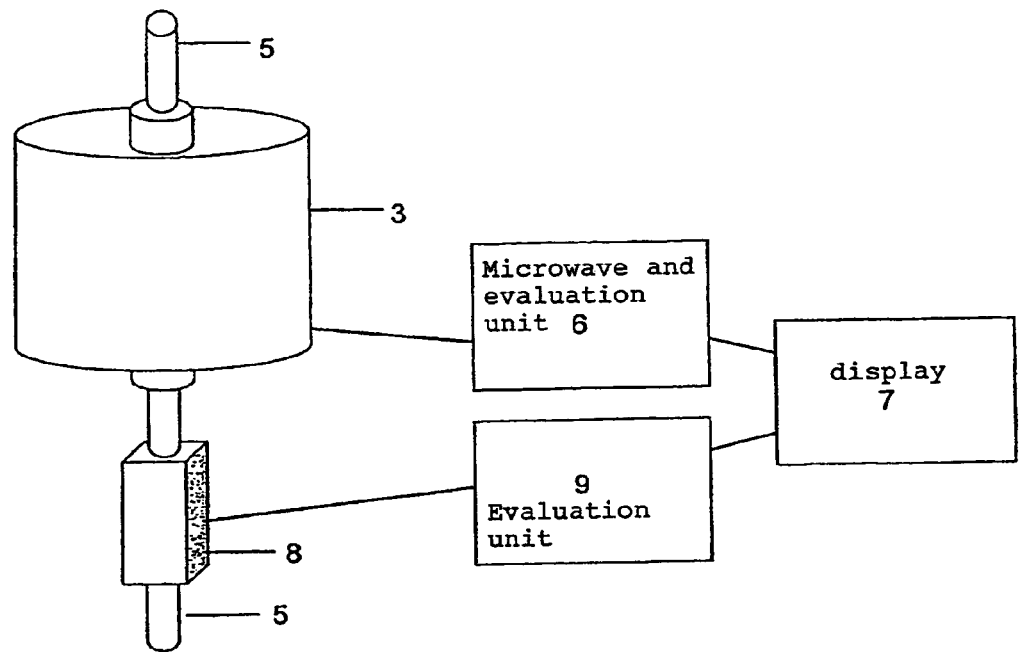
FIG. 7 shows a further embodiment with which a method can be carried out.

FIG. 7 schematically shows the structure of the measuring system. The capsules pass, in the tube 5, firstly through an integrating sensor 3, which is used to determine the total mass and the total moisture of the capsules with the aid of the microwave and evaluation unit 6. The moisture of the capsule casing is determined by an infrared radiator and detector 8 using evaluation electronics 9. The result is again calculated and displayed in the unit 7.

4. Combination of a Microwave Resonator for Profile Measurement with a Device for Measuring the Speed of the Capsules When using a simple microwave profile resonator 4, there is also the possibility of acquiring four measured values in order to be able to determine the four unknown quantities mentioned above. In this case, the resonant frequency displacement and the broadening of the resonance curve have to be determined by integration of the microwave signals over the entire capsule. Since these integrals are speed-dependent, the capsule speed can be determined and taken into account in obtaining the integrals by a suitable measuring method (e.g. optical Doppler radar method). The measured values $A_{int}$ and $B_{int}$ are thus determined in this case as follows:

$$A_{int} = \int_0^T A \cdot V dt \quad (11)$$

$$B_{int} = \int_0^T B \cdot V dt \quad (12)$$

Designations:
- $A_{int}$ resonant frequency displacement through entire capsule
- $B_{int}$: broadening of the resonance curve through entire capsule A: local resonant frequency displacement
B: local broadening of the resonance curve
V: capsule speed The integration takes place here over the entire time during which the capsule is situated in the measuring field, i.e. from entering the field at t=0 until leaving the field at t=T.

Figure 6:
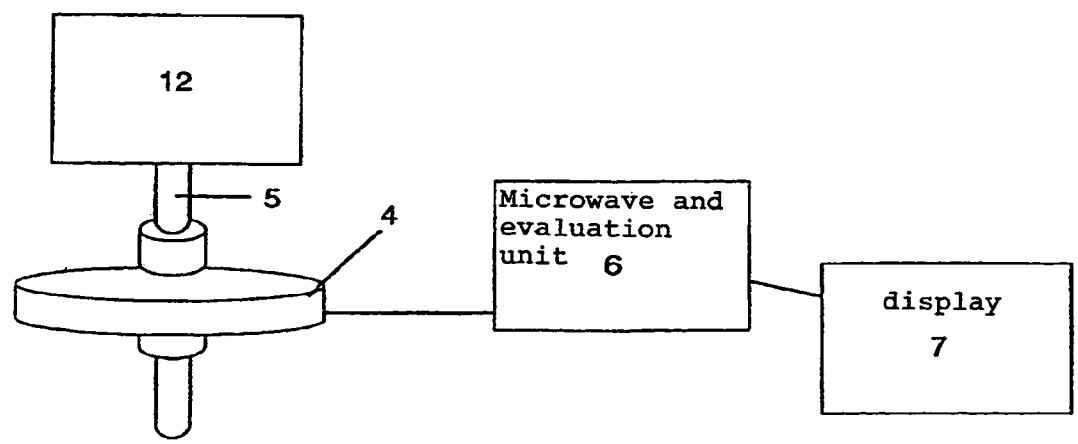
FIG. 6 shows yet another apparatus with which a method can be carried out.

Besides determination of $A_{int}$ and $B_{int}$ according to relations (11) and (12), it is also possible to obtain the microwave moisture values $F_{ki}$ and $F_k$ from the profile (see FIG. 2). The capsule contents are again calculated by solving the system of equations (4)-(7). Given a constant moisture of the capsule contents, in this case, too, the reduced system of equations (8)-(10) has to be solved. In this case, too, the measurement of the mass of the contents $m_i$ is only possible with partially filled capsules. A schematic diagram of the measuring system is shown in FIG. 6. The capsules are again moved through the tube 5 through a profile sensor 4. This can be effected, for example, by an air flow. Using a measuring device 10 the speed of the capsules is determined, and evaluated at 11. The display again takes place in the unit 7, after evaluation and integration of the microwave signal in the unit 6.

5. Microwave Resonator for Profile Measurement on Guidance Through the Resonator at Constant Speed The use of a simple microwave profile resonator without a combined speed measurement of the capsules is possible if it can be ensured that the capsules always have the same speed on conveyance through the resonator. In this case, the speed does not need to be taken into account in obtaining the integrals to determine $A_{int}$ and $B_{int}$:

$$A_{int} = \int_0^T A\,dt \quad (13)$$

$$B_{int} = \int_0^T B\,dt \quad (14)$$

Designations:
- $A_{int}$: resonant frequency displacement through entire capsule
- $B_{int}$: broadening of the resonance curve through entire capsule
- A: local resonant frequency displacement
- B: local broadening of the resonance curve The integration takes place here over the entire time during which the capsule is situated in the measuring field, i.e. from entering the field at t=0 until leaving the field at t=T.

Besides determination of $A_{int}$ and $B_{int}$ according to relations (11) and (12), it is also possible to obtain the microwave moisture values $F_{ki}$ and $F_k$ from the profile (see FIG. 2). The capsule contents are again calculated by solving the system of equations (4)-(7). Given a constant moisture of the capsule contents, in this case, too, the reduced system of equations (8)-(10) has to be solved. In this case, too, the measurement of the mass of the contents $m_i$ is only possible with partially filled capsules.

FIG. 6 schematically shows an apparatus for carrying out the method. A unit arranged at 12 ensures that the capsules pass through the tube 5 at a uniform and known speed. They are then measured by the profile sensor 4 and the microwave and evaluation electronics 6. The result is again calculated and displayed in the unit 7.

The disclosed methods and apparati have applicability in connection with measuring with the aid of microwaves the mass and/or moisture of the contents of capsules which may be filled or incompletely filled and contain products such as medicinal products, pharmaceutical products, vitamins and similar products.

The invention claimed is:

1. Method for measuring the mass and/or moisture of the contents of incompletely filled capsules having a longitudinal extent and containing products, with the aid of microwaves, in which method the displacement of the resonant frequency and broadening of the resonance curve caused by the capsules in at least two resonators is determined and evaluated, a first resonator with a first measuring field which is homogeneous over the capsule dimensions being used to determine the total mass/moisture of the capsule and contents, wherein the contents of the capsule are transported to one side of the capsule cavity by acceleration or gravity, and in that a second resonator with a second measuring field with a local resolution less than the longitudinal extent of the capsules is used to determine location-dependent profiles of mass/moisture values while each capsule is moving through said second measuring field, the displacement of the resonant frequency and broadening of the resonance curve of the first and second resonators are combined to determine the mass and/or moisture of the contents of the capsules.

2. The method of claim 1, wherein the moisture of the capsule casing is determined with the aid of infrared radiation.

3. Method according to claim 2, wherein the measurements are carried out at a microwave frequency of 1 to 50 GHz.

4. The method of claim 1, wherein the speed at which the capsule is moved through the measuring field is measured, and in that the total mass/moisture of the capsule is determined by integration.

5. Method according to claim 4, wherein the moisture of the capsule is determined with the aid of microwaves as a function of the measuring point over the length of the capsule.

6. Method according to claim 4, wherein the measurements are carried out at a microwave frequency of 1 to 50 GHz.

7. The method of claim 1, wherein all the capsules are moved at the same speed through the measuring volume and the total mass/moisture of the capsules is determined by integration.

8. Method according to one of claim 7, wherein the moisture of the capsule (1) is determined with the aid of microwaves as a function of the measuring point over the length of the capsule.

9. Method according to claim 7, wherein the measurements are carried out at a microwave frequency of 1 to 50 GHz.

10. Method according to claim 1, wherein the moisture of the capsule is determined with the aid of microwaves as a function of the measuring point over the length of the capsule.

11. Method according to claim 1, wherein the measurements are carried out at a microwave frequency of 1 to 50 GHz.

12. Method according to claim 1, wherein the measurements are carried out at a microwave frequency of 1 to 5 GHz.

13. Apparatus for measuring the mass and/or moisture of the contents of capsules having a length and containing products, with the aid of microwaves, said apparatus having a first microwave resonator with a first measuring field which is homogeneous over the extent of the capsule, wherein the apparatus has devices for transporting the contents of the capsule to one side of the capsule cavity by acceleration or gravity and a second microwave resonator for measuring a mass and/or moisture profile of each capsule with a second measuring field which has a local resolution less than the capsule length, said apparatus including evaluation electronics connected to measure changes in said first and second measuring fields caused by capsules moving through said first and second measuring fields, said changes in said first and second measuring fields being combined to determine the mass and/or moisture of the contents of the capsules.

14. The apparatus of claim 13, wherein the apparatus comprises infrared measuring devices for measuring the moisture of the capsule casing.

15. Apparatus according to claim 14, wherein it is operable at microwave frequencies of 1 to 50 GHz.

16. The apparatus of claim 13, wherein the apparatus has devices for transporting the contents of the capsule to one side of the capsule cavity by acceleration or gravity and a device for conveying the capsules at constant speed.

17. Apparatus according to claim 16, wherein it is operable at microwave frequencies of 1 to 50 GHz.

18. Apparatus according to claim 13, wherein it is operable at microwave frequencies of 1 to 50 GHz.

19. Apparatus according to claim 13, wherein it is operable at microwave frequencies of 1 to 5 GHz.

20. A method for measuring the mass of product contained in capsules with the aid of microwaves, said capsules peripherally bounded by a casing having dimensions and defining an interior space, said method comprising:
  measuring the total mass/moisture of each capsule and its contents with a first resonator having a first measuring field having a first resonant frequency and a first resonance curve and which is homogeneous over a first measuring volume at least as great as the casing dimensions, said step of measuring including:
    positioning each said capsule in said first measuring field; and
    detecting displacement of the first resonant frequency and broadening of the first resonance curve while said capsule is present in said first measuring field;
  measuring the mass and/or moisture of the capsule with a second resonator having a second measuring field with a second resonant frequency and a second resonance curve, said second resonator constructed and energized so that said second measuring field is concentrated at the periphery of said capsule so that only a portion of the casing is detected and the product contained in the capsule does not substantially influence said second measuring field, said step of measuring including:
    positioning each said capsule in said second measuring field in a known orientation where said casing is present in said second measuring field; and
    detecting displacement of said second resonant frequency and broadening of said second resonance curve while said casing is present in said second measuring field; and
  calculating the mass of product contained in each capsule using the displacement of said first and second resonant frequencies and the broadening of said first and second resonance curves.

21. Method according to claim 20, wherein the measurements are carried out at a microwave frequency of 1 to 50 GHz.

22. An apparatus for measuring the mass of product contained in capsules with the aid of microwaves, said capsules peripherally bounded by a casing having dimensions and defining an interior space and moved through said apparatus along a pre-determined path, said apparatus comprising:
  a first resonator having a first measuring field having a first resonant frequency and a first resonance curve and which is homogeneous over a first measuring volume at least as great as the casing dimensions;
  a second resonator having a second measuring field with a second resonant frequency and a second resonance curve, said second measuring field being restricted to a volume less than said first measuring volume so that only a portion of the casing is detected and the product contained in the capsule does not substantially influence said second measuring field;
  a conveyor arranged to move said capsules through said apparatus along said pre-determined path passing through said first and second measuring fields and to maintain the capsules in a known orientation with respect to at least said second measuring field; and
  measurement electronics operatively connected to said first and second resonators to detect displacement of the first resonant frequency and broadening of the first resonance curve caused by the presence of a capsule and its contents in said first measuring field and displacement of said second resonant frequency and broadening of said second resonance curve caused by the presence of the casing of said capsule in said second measuring field,
  wherein the displacement of said first and second resonant frequencies and the broadening of said first and second resonance curves are used to calculate the mass of product contained in said capsule.

23. The apparatus of claim 22, wherein the apparatus has devices for transporting the contents of the capsule to one side of the capsule cavity by acceleration or gravity and a device for measuring the speed of the capsules.

24. Apparatus according to claim 23, wherein it is operable at microwave frequencies of 1 to 50 GHz.

25. Apparatus according to claim 22, wherein it is operable at microwave frequencies of 1 to 50 GHz.

* * * * *